United States Patent [19]

Rowland

[11] Patent Number: 5,782,232
[45] Date of Patent: Jul. 21, 1998

[54] MEDICAL NEBULISER

[76] Inventor: Stephen James Rowland, 52 Broadlands Avenue, Sheffield S19 6RL, Great Britain

[21] Appl. No.: 765,804
[22] PCT Filed: Jun. 26, 1995
[86] PCT No.: PCT/GB95/01494
  § 371 Date: Jan. 14, 1997
  § 102(e) Date: Jan. 14, 1997
[87] PCT Pub. No.: WO96/02293
  PCT Pub. Date: Feb. 1, 1996

[30] Foreign Application Priority Data

Jul. 16, 1994 [GB] United Kingdom ............ 9414399

[51] Int. Cl.$^6$ .................................. B05B 3/02
[52] U.S. Cl. .................... 128/200.14; 128/200.17
[58] Field of Search .................... 239/223, 224, 239/338; 128/200.14, 200.17, 200.21

[56] References Cited

U.S. PATENT DOCUMENTS

| 2,166,772 | 7/1939 | Salsas-Serra | 239/224 |
| 2,357,833 | 1/1944 | Joos | 128/200.17 |
| 5,203,506 | 4/1993 | Gross et al. | 239/224 |

FOREIGN PATENT DOCUMENTS

| 1026736 | 7/1985 | U.S.S.R. | 239/223 |
| 751609 | 7/1956 | United Kingdom | 239/224 |

*Primary Examiner*—Vincent N. Millin
*Assistant Examiner*—Robert Wieland
*Attorney, Agent, or Firm*—Trexler, Bushnell, Giangiorgi & Blackstone, Ltd.

[57] ABSTRACT

Disclosed is a medical nebuliser including a container providing a sump area for a liquid drug. A rotor is located in the container, and an impacter ring encircles the rotor. The rotor is formed from two disc shaped components at least one of which is concave. The components have co-operating mating faces machined so that when they are clamped together, microscopic passageways are provided therebetween. There is a connection between the interior of the rotor and a sump to contain liquid to be nebulised. The impacter ring has an impacter face that is an inwardly facing frusto-conical surface to encourage the return of larger droplets to the sump. The frusto-conical surface has a number of ridges in the form of concentric or helical grooves over its length, whereby there is the ejection of liquid drug from within the perpendicular to the axis of rotation of the rotor, of uniform and controlled droplet size which impacts on the ridges on the impacter ring to reduce the droplet size of liquid drug.

3 Claims, 1 Drawing Sheet

MEDICAL NEBULISER

This invention relates to a medical nebuliser.

In the field of the production of aerosols or so-called micro-fogs it is known that such as for as example in French Patent 75220 to provide a revolving plate construction to which can be fed a fluid, the fluid being spread into a film and ejected from the plate against a knurled ring whereby to produce an aerosol. In such a construction there is no control over the fluid as it is ejected from the plate and consequently on being broken up by the knurled ring, the fluid is in the form of droplets of a totally uncontrolled size or range of sizes.

Such a construction is unsuited to use as a medical nebuliser, a well-known device used to produce a nebulised aerosol of a liquid soluble drug, in order to administer that drug, via the inhaled route, to the lungs of the patient.

Medical nebulisers in current production produce the aerosol by one of two methods i.e. by compressed air or other inhaleable gas passed through a small orifice nebulising the liquid by a venturi effect, or by ultrasonic vibration. The compressed gas powered units are noisy and generally operated by mains electricity or substantial rechargeable batteries, and the units are consequently bulky and heavy. Ultrasonic devices, though quieter and smaller, are relatively expensive.

The object of the invention is to provide a medical nebuliser that avoids those disadvantages mentioned above.

According to the present invention, a medical nebuliser comprising a container providing a sump area for a liquid drug, a hollow rotatable means located in the chamber, and an impacter ring encircling the rotatable means, characterized in that the rotatable means is a rotor formed from two disc shaped components at least one of which is concave, the mating faces of the components being so machined that when they are clamped together miscoscopic passageways are provided between their mating faces and there being a connection between the interior of the rotor and a sump to contain liquid to be nebulised, the impacter ring having an impacter face that is angular to encourage the return of larger droplets to the sump, the angular face having a number of ridges in the form of concentric or helical grooves over its length, whereby there is the ejection of liquid drug from within the perpendicular to the axis of rotation of the hollow rotatable means, of uniform and controlled droplet size which impacts on the ridges on the impacter ring to reduce the droplet size of liquid drug.

By the nature of the one or both component having a concave cross-section (and this or these faces positioned together) the rotor so created is hollow. The rotor is fed via a feed pipe from a sump containing the solution of drug to be nebulised. By virtue of the clamping of the machined surfaces (with or without structured radial grooves) of the rotor only microscopic passageways are present between the surfaces, but under the high pressures generated within the rotor the liquid to be nebulised is drawn into the rotor from from the sump and forced to the periphery of the rotor and ejected from the rotor as an aerosol. These droplets ejected tangentially from the rotor impact on the inner surface of the impacter ring supported in the plane of flight of the fast moving droplets. This impacter ring is so designed as to cause further droplet breakdown and yield droplets of the required size.

To provide for the driving of the drum or rotor, an appropriate motor is provided in a housing located on the container. The bottom of the housing has one or more orifices which act as an air inlet to the container and the outlet from the container may have a detachable mouthpiece or mask to allow the nebulised aerosol to be inhaled. The inlet and outlet to the container may be provided with valves. The valve arrangement allows the nebulised aerosol to be delivered to the mouthpiece or mask only during inspiration therefore allowing smaller doses of drug to be used.

With the impact face on the impacter ring angular to encourage the return of larger droplets to the sump, and formed with ridges, it avoids the need for total accuracy of alignment of the tangential discharge plane of the droplets and the impacter ring, a number of ridges may be provided across the impact face of the impacter ring, such as by providing concentric or helical grooves. In an alternative form of construction the impact face is formed as a stepped configuration with a number of vertical walls connected by horizontal ledges.

A specific embodiment of the invention will now be described, by way of example, with reference to the accompanying drawings, in which.

Figure 1:
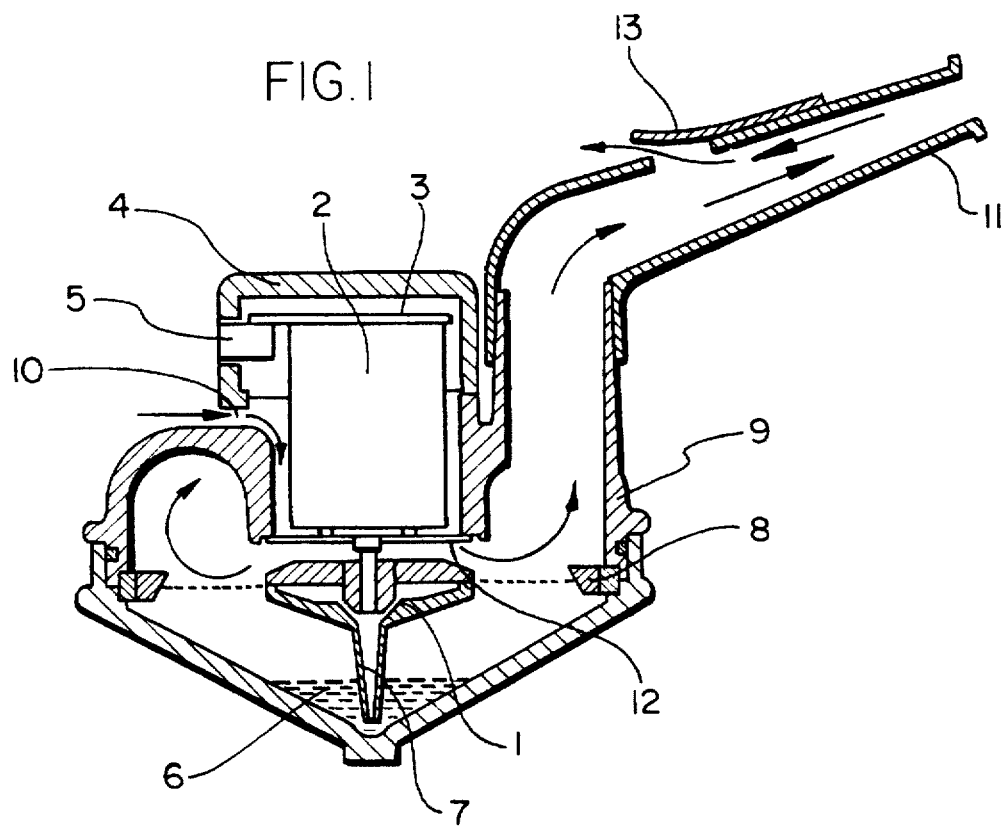
FIG. 1 shows a longitudinal section of such a device.

In FIG. 1 a rotor 1 is driven by a high speed electric motor 2. The motor is fixed by a flexible material 3 to the upper housing 4 allowing vibration to be minimised and motor speed optimised. The motor 2 is powered by a direct current source via socket 5. The rotor 1 is fed with the liquid 6 to be nebulised by means of a narrow angled conical tube 7 by centrifugal force. The droplets formed by rotation of the rotor 1 are tangentially ejected from the rotor and impact on the impacter ring 8. The nebulised aerosol is contained in the containment vessel 9. Air can be entrained through orifice 10 and the nebulised aerosol inhaled by the patient through the mouthpiece 11. By means of the inlet valve 12 and the mouthpiece 11 the nebulised aerosol is inhaled through the device and exhalation to atmosphere is allowed through outlet valve 13.

Figure 2:
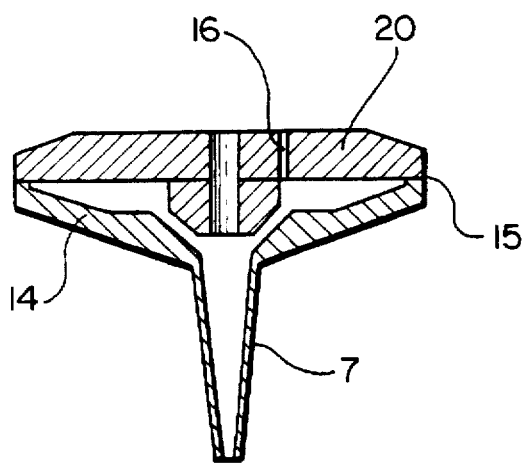
FIG. 2 shows an enlarged section of the rotor.

As is shown by FIG. 2, the rotor comprises two parts. The upper component 20 is secured to the shaft of the driving motor. To this the lower component 14 is fixed so as to provide a secure abutting fit at the periphery 15 of the rotor. The liquid to be nebulised is drawn into the interior of the rotor via a conical feedpipe 7. The upper component has a vent hole 16 close to its centre of rotation to allow the rotor to self-prime.

Figure 3:
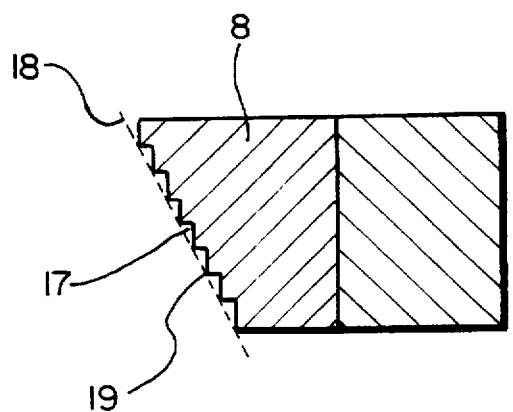
FIG. 3 shows an enlarged section of the impacter ring.

FIG. 3 shows the impacter ring 8 to comprise a helical groove 17 fashioned on the inner, downwardly facing surface 18. In this way some of the droplets produced by the rotor impact on the square edges 19 of the ring and consequently are broken down even further into the smaller droplets required for medical inhalation, and there is avoided the need for absolute accuracy of alignment of the tangential discharge plane of droplets from the rotor and the impacter ring.

I claim:

1. A medical nebuliser comprising a container providing a sump area for a liquid drug, a rotor located in the container, and an impacter ring encircling the rotor, the rotor being formed from two disc shaped components at least one of which is concave, the components having co-operating mating faces being so machined that when they are clamped together microscopic passageways are provided between their mating faces, and there being a connection between an interior of the rotor and a sump to contain liquid to be nebulised, the impacter ring having an impacter face that is an inwardly facing frusto-conical surface to encourage the return of larger droplets to the sump, the frusto-conical surface having a number of ridges in the form of concentric or helical grooves over its length, whereby there is the ejection of liquid drug from within the perpendicular to the axis of rotation of the rotor, of uniform and controlled droplet size which impacts on the ridges on the impacter ring to reduce the droplet size of liquid drug.

2. A medical nebuliser as in claim 1, further comprising an appropriate motor to drive the rotor.

3. A medical nebuliser as in claim 1 wherein the impact face of the impacter ring is formed as a stepped configuration with a number of vertical walls connected by horizontal ledges.

* * * * *